(12) United States Patent
Williams

(10) Patent No.: US 6,920,361 B2
(45) Date of Patent: Jul. 19, 2005

(54) REVERSE WOUND ELECTRODES

(75) Inventor: Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 173 days.

(21) Appl. No.: 10/367,211

(22) Filed: Feb. 14, 2003

(65) Prior Publication Data

US 2004/0162600 A1 Aug. 19, 2004

(51) Int. Cl.⁷ .......................... A61N 1/05; A61B 5/0408
(52) U.S. Cl. ..................... 607/122; 607/116; 600/373; 600/374
(58) Field of Search ................... 607/115–156; 600/373–382; 606/41–50

(56) References Cited

U.S. PATENT DOCUMENTS

| | | | |
|---|---|---|---|
| 3,572,344 A | | 3/1971 | Bolduc |
| 4,149,104 A | * | 4/1979 | Yoshimori ............. 313/340 |
| 4,437,474 A | | 3/1984 | Peers-Trevarton |
| 4,776,334 A | * | 10/1988 | Prionas ................. 606/42 |
| 5,454,839 A | * | 10/1995 | Anderson et al. ......... 607/123 |
| 5,582,609 A | | 12/1996 | Swanson et al. |
| 5,649,974 A | | 7/1997 | Nelson et al. .......... 607/122 |
| 5,810,887 A | * | 9/1998 | Accorti et al. ......... 607/122 |
| 5,824,026 A | * | 10/1998 | Diaz .................. 607/116 |
| 5,841,932 A | | 11/1998 | Page et al. |
| 5,935,160 A | | 8/1999 | Auricchio et al. |
| 5,950,956 A | | 9/1999 | Yukitake |
| 5,951,471 A | | 9/1999 | de la Rama et al. ...... 600/381 |
| 6,041,832 A | | 3/2000 | Miyawaki et al. |
| 6,210,395 B1 | | 4/2001 | Fleischhacker et al. .... 604/526 |
| 6,212,434 B1 | | 4/2001 | Scheiner et al. ........ 607/123 |
| 6,278,355 B1 | | 8/2001 | Hopkinson et al. |
| 6,477,427 B1 | | 11/2002 | Stolz et al. |
| 6,516,230 B2 | | 2/2003 | Williams et al. |
| 2002/0003936 A1 | | 1/2002 | Kaliszek |
| 2002/0183818 A1 | | 12/2002 | Williams et al. |

FOREIGN PATENT DOCUMENTS

| | | | | |
|---|---|---|---|---|
| JP | H02-196054 | 3/1994 | ......... | A61M/25/01 |
| WO | WO 00/27470 | 5/2000 | ......... | A61N/1/05 |
| WO | WO 02/32500 A1 | 4/2002 | ......... | A61N/1/05 |

* cited by examiner

*Primary Examiner*—Jeffrey R. Jastrzab
(74) *Attorney, Agent, or Firm*—Girma Wolde-Michael

(57) ABSTRACT

An implantable lead includes an insulative sheath and a coil member; the coil member including a conductor wound from a proximal end of the coil member to a distal end and reverse wound back toward the proximal end to form an electrode on an outer diameter of the coil member adjacent and distal to the insulative sheath.

8 Claims, 11 Drawing Sheets

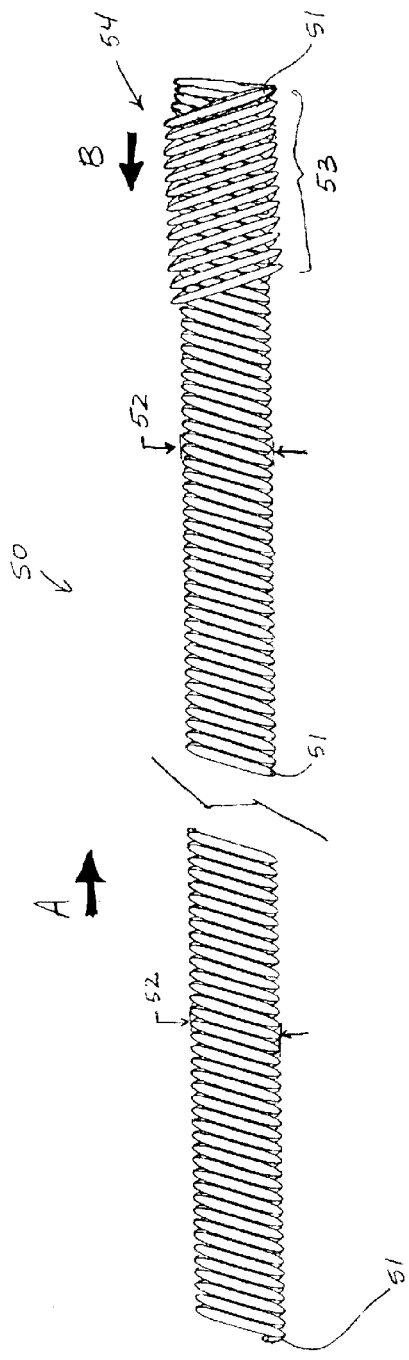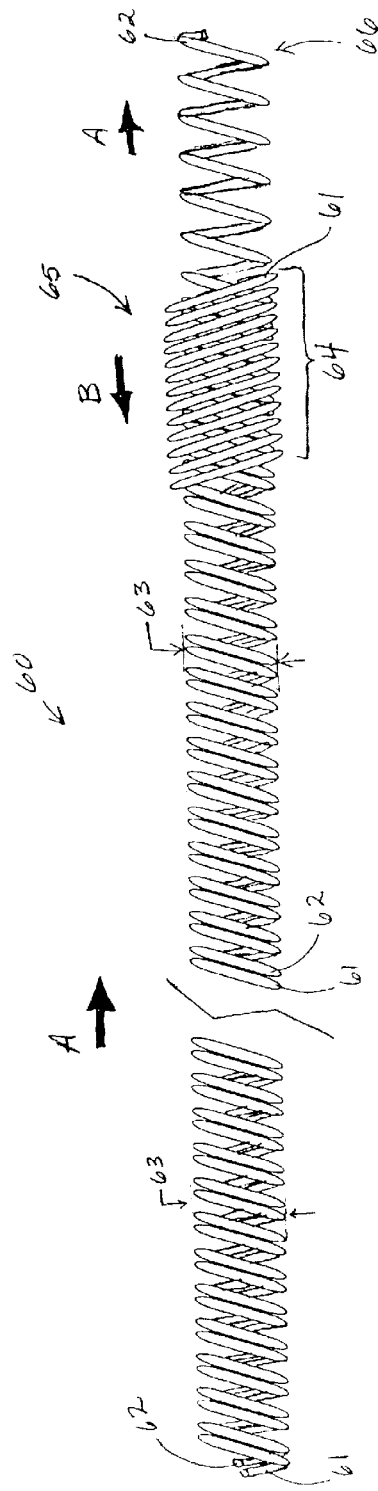
FIGURE 1A
FIGURE 1B

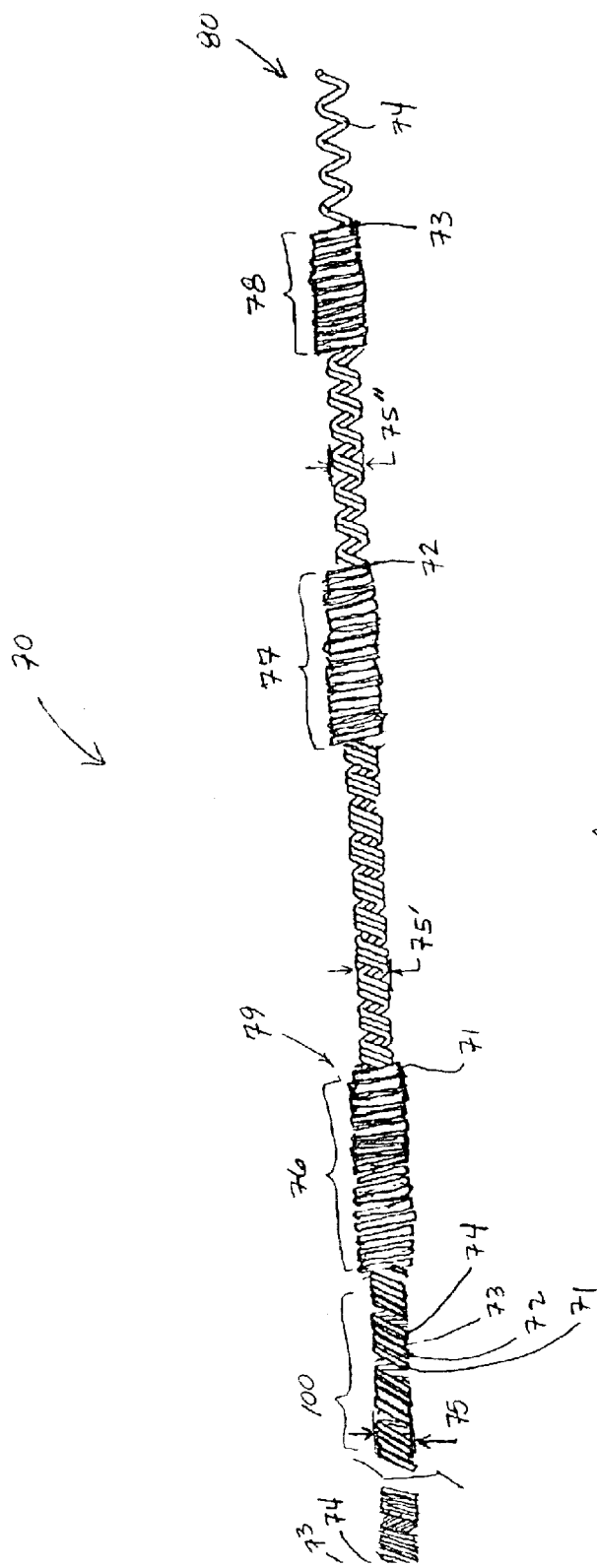

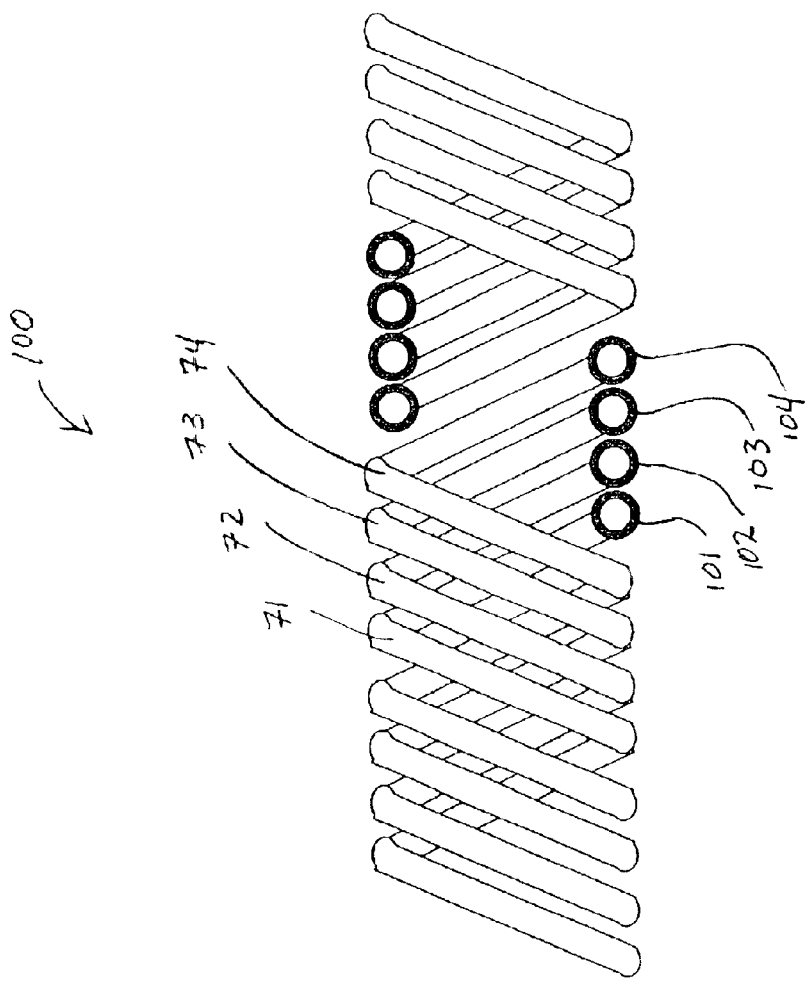

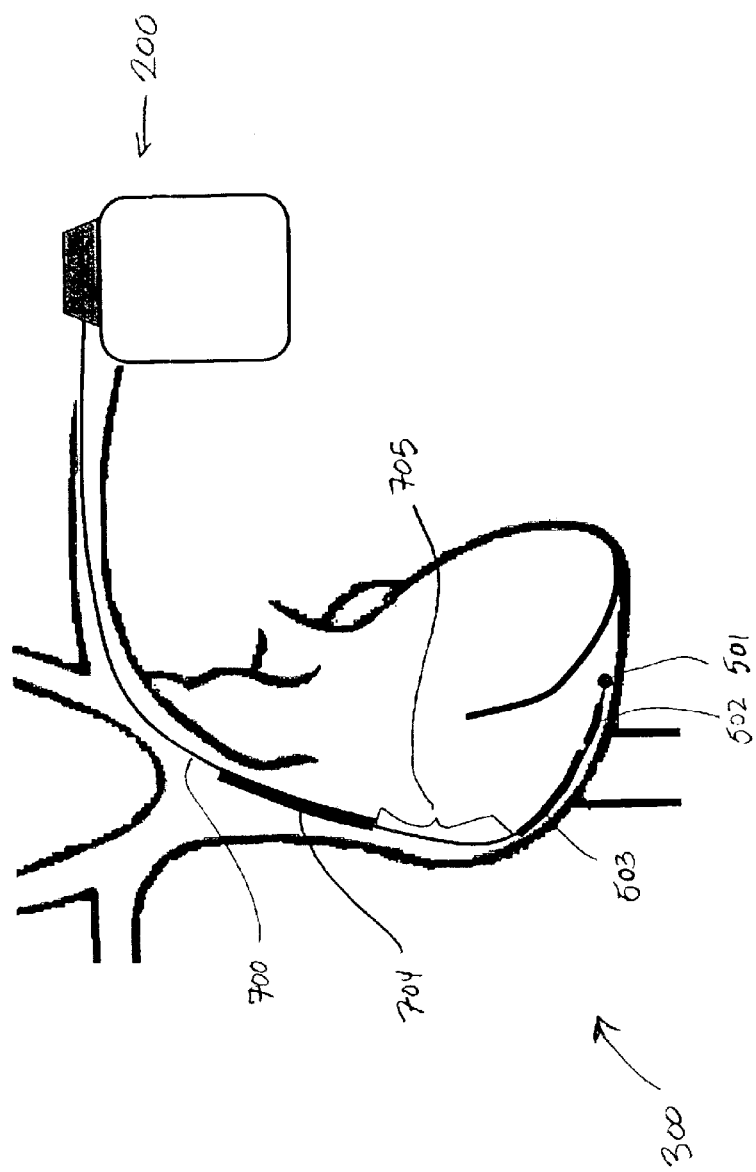

REVERSE WOUND ELECTRODES

FIELD OF THE INVENTION

This invention relates to implantable devices and more particularly relates to the design and manufacture of implantable leads.

BACKGROUND OF THE INVENTION

In the traditional forming of implantable medical electrical leads, one or more wires are wound on a mandrel so as to form a coil. The wires are wrapped with enough tension to cause the wires to exceed their yield point and thus to hold a coiled shape. The pitch of a coil may range from close wound, that approaching the wire diameter or the sum of the wire diameters, for multi-wire coils, to space wound, that exceeding the wire diameter or sum of the wire diameters. The coil may be one of several conductors included in an implantable lead body and the coil may be formed from multiple insulated wires as a multi-conductor coil. The lead body is usually constructed having an outer polymeric sheath encasing the conductors, which may be arranged coaxially or co-linearly and are insulated from one another. A distal end of each conductor is coupled to one or more electrodes while a proximal end of each conductor is coupled to a contact of a connector that is in turn coupled to an implantable pulse generator (IPG) or an implantable cardioverter defibrillator (ICD). The distal end of the lead is implanted to be positioned within the heart so that the electrodes may deliver pacing and or defibrillation therapy by both sensing electrical activity of the heart muscle and stimulating the heart muscle.

Each conductor is typically coupled to a corresponding electrode, which has been formed as a separate component, such as a ring electrode, a coil electrode or a tip electrode. In designing and constructing joints between the conductors and the electrodes care must be taken to form reliable mechanical and electrical coupling; it is also desirable that the joints do not increase the profile of the lead body. Eliminating as many joints as is practical in the construction of a lead may improve the reliability of the lead and increase the ease of manufacturing.

BRIEF DESCRIPTION OF THE DRAWINGS

FIG. 1A is a plan view of a coil according to one embodiment of the present invention.

FIG. 1B is a plan view of a multi-conductor coil according on one embodiment of the present invention.

FIG. 1C is a plan view of a multi-conductor coil according to another embodiment of the present invention.

FIG. 1D is a partial section plan view of the multi-conductor coil of FIG. 1C.

DETAILED DESCRIPTION OF THE PREFERRED EMBODIMENTS

Figure 2A:
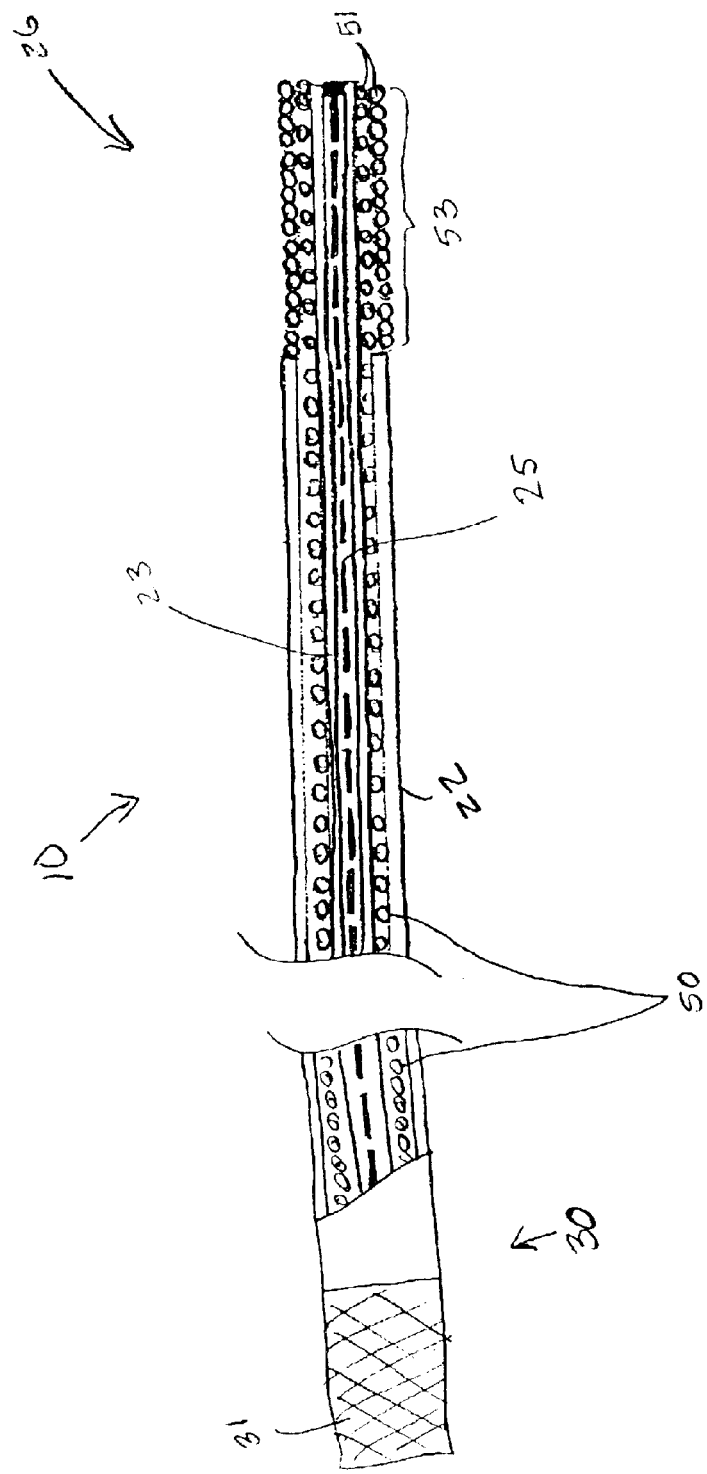
FIG. 2A is a partial section plan view of an implantable lead incorporating the coil from FIG. 1A.

The following detailed description is to be read with reference to the figures, in which like elements in different figures have like reference numerals. The figures, which are not necessarily to scale, depict selected embodiments and are not intended to limit the scope of the invention. Embodiments of the present invention may be employed in many various types of devices, such as pacemakers, cardioverter defibrillators, and neurostimulators, for treating patient medical conditions. Skilled artisans will recognize that the examples provided herein have many useful alternatives that fall within the scope of the invention.

Figure 2B:
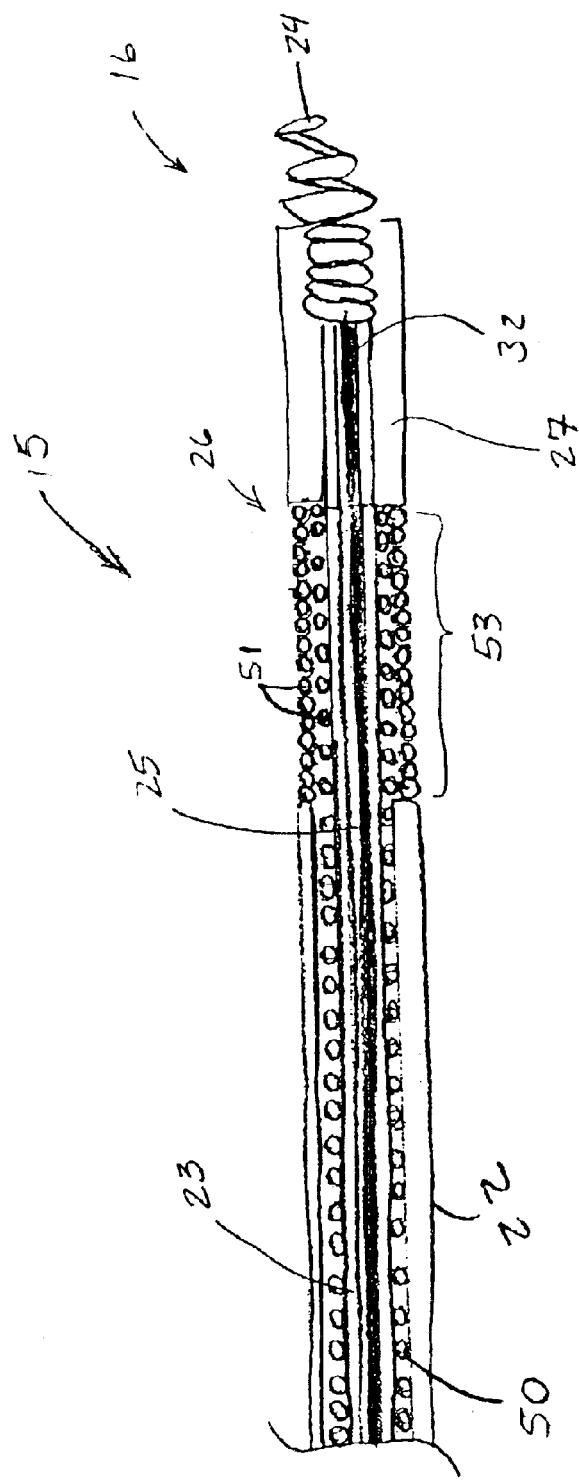
FIG. 2B is a cross-sectional plan view of a distal end of an alternate embodiment of a lead incorporating the coil from FIG. 1A

FIG. 1A is a plan view of a coil 50 according to one embodiment of the present invention. Coil 50 is incorporated into embodiments of medical electrical leads according to the present invention as illustrated in FIGS. 2A and 2B. As illustrated in FIG. 1A, coil 50 includes a wound conductor 51 and an electrode 53 at a distal end 54; wound conductor 51 forming an outer diameter 52 of coil 50 and a reverse wound portion of conductor 51, over outer diameter 52, forming electrode 53. Coil 50 may be formed using a programmable coil winder, known to those skilled in the art, winding in a first direction "A" and then reverse winding in a second direction "B" to form electrode 53 over outer diameter 52. Conductor 51 and all other conductors presented herein for alternate embodiments are formed from any material capable of reliably conducting electrical current after having been subjected to numerous repetitive bending and torsional stresses, examples of such materials include tantalum, MP35-N alloy, platinum, Elgiloy, and stainless steel. Conductor 51 and all other conductors illustrated herein in various embodiments include a single wire, however, in alternate embodiments, a conductor includes a plurality of common wires; anywhere from two to six wires, depending on the application, per conductor are contemplated. Furthermore, alternate embodiments include composite wires formed of any of the preceding metals and including a silver or gold core. Because the reverse wound portion of conductor 51 serves as electrode 53, an outer surface of the reverse wound portion of conductor 51, as well as outer surfaces of all reverse wound portions of conductors forming electrodes in various embodiments presented herein, must be suitable for this purpose; a platinum or platinum iridium surface is one example of a suitable electrode surface known to those skilled in the art. In one embodiment, a platinum clad wire is used for conductor 51, in another embodiment a platinum-iridium wire is used and, in yet another embodiment, a platinum surface is formed, for example, by sputtering platinum over reverse wound portion of conductor 51 forming electrode 53.

Figure 3:
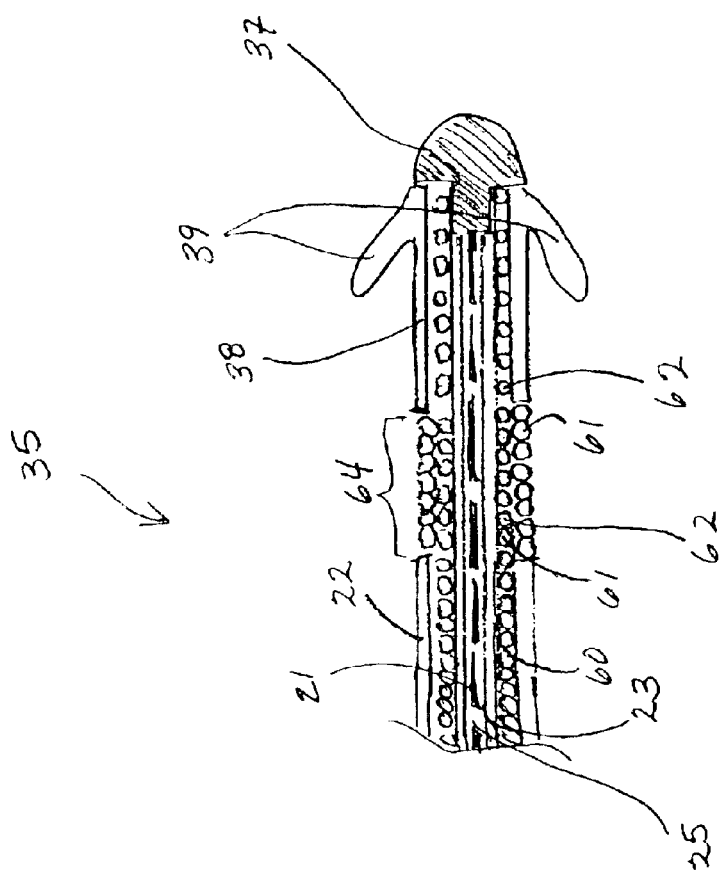
FIG. 3 is a cross-sectional plan view of a distal end of an alternate embodiment of a lead incorporating the coil from FIG. 1B

FIG. 1B is a plan view of a multi-conductor coil 60 according to one embodiment of the present invention. Coil 60 is incorporated into an embodiment of a medical electrical lead according to the present invention as illustrated in FIG. 3. As illustrated in FIG. 1B coil 60 includes a first wound conductor 61, a second wound conductor 62, forming an outer diameter 63 of coil, and an electrode 64 at a first distal end 65; first conductor 61 includes a reverse wound portion forming electrode 64, over outer diameter 63, and second conductor 62 extends beyond electrode 64 to a second distal end 66. Coil 60 may be formed using a programmable coil winder, known to those skilled in the art, winding conductors 61 and 62 in first direction "A" and then reverse winding first conductor 61 in second direction "B" to form electrode 64, while continuing to wind second conductor 62 in direction "A" to second distal end 66. It should be noted that an outer diameter and pitch of coil 60 between first distal end 65 and second distal end 66 need not be the same as a pitch or outer diameter 63 of coil 60 indicated proximal to electrode 64. According to one embodiment of the present invention, second conductor 62 is joined to an electrode tip at second distal end 66, such as tip electrode 37, illustrated in FIG. 3, therefore second conductor 62 must be electrically isolated from first conductor 61. Either first conductor 61 or second conductor 62, or both, include an outer insulative layer according to embodiments of the present invention, such insulative layers being described in conjunction with FIG. 1D.

Figure 4:
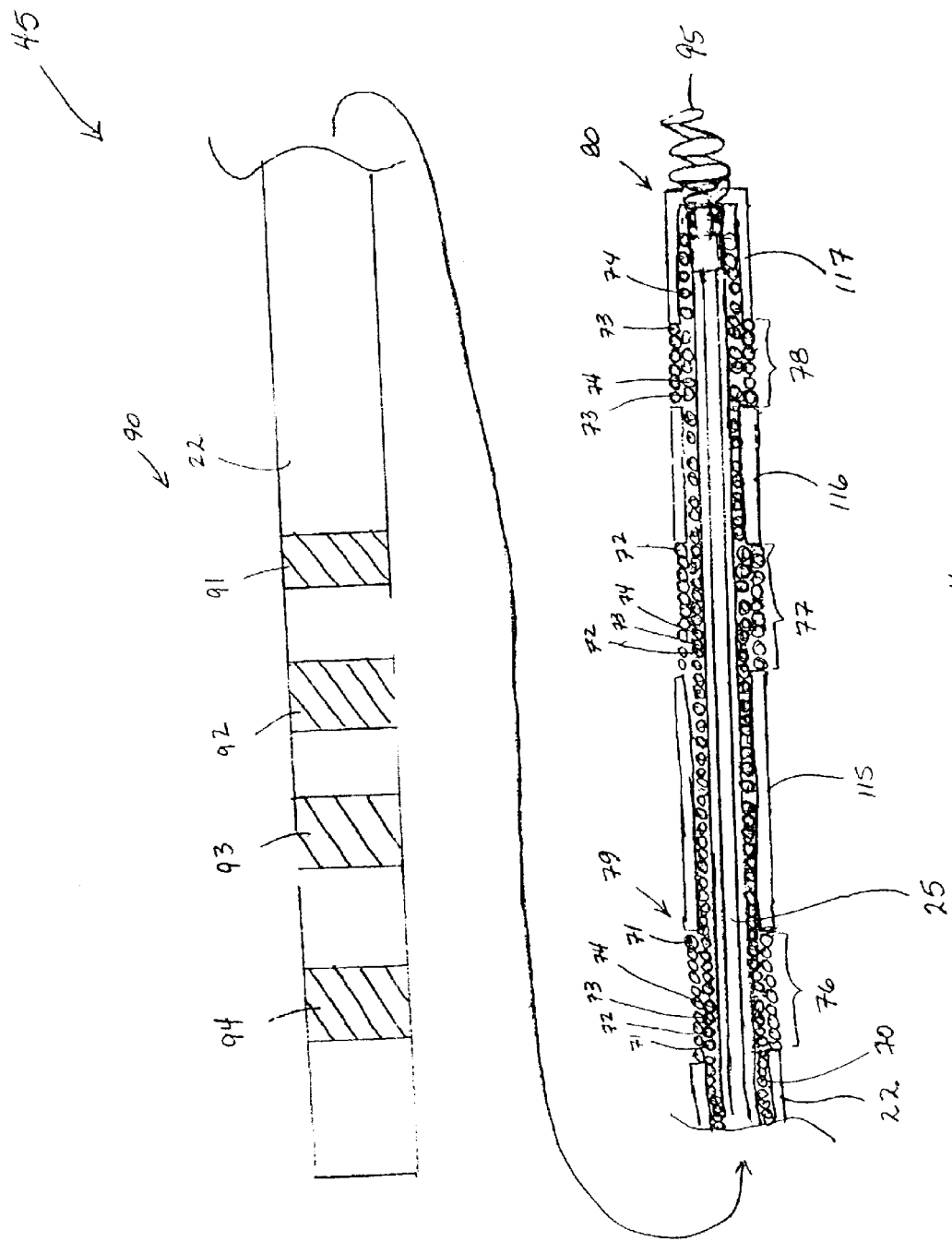
FIG. 4 is a partial section plan view of a lead incorporating the coil from FIGS. 1C–D FIGS. 5–8 are schematics depicting several embodiments of implantable leads according to the present invention joined to an implantable medical device and implanted in exemplary locations within a heart.

FIG. 1C is a plan view of a multi-conductor coil 70 according to another embodiment of the present invention. Coil 70 is incorporated into an embodiment of a medical electrical lead according to one embodiment of the present invention as illustrated in FIG. 4. As illustrated in FIG. 1C, coil 70 includes a first wound conductor 71, a second wound conductor 72, a third wound conductor 73, and a fourth wound conductor 74, all forming an outer diameter 75; coil 70 further includes a first electrode 76, a first intermediate electrode 77, and a second intermediate electrode 78. First electrode 76 is formed by reverse winding first conductor 71 over outer diameter 75 at a first distal end 79 and fourth conductor extends to a second distal end 80. In between first distal end 79 and second distal end 80 second and third conductors 72 and 73 are reverse wound to form first and second intermediate electrodes 77 and 78 over outer diameters 75' and 75", respectively, as illustrated in FIG. 1C. In one embodiment diameters 75' and 75" are approximately equal to diameter 75, however in an alternate embodiment diameter 75' is smaller than diameter 75 and diameter 75" is smaller than diameter 75'. Coil 70 may be formed in generally the same manner described for coil 60 illustrated in FIG. 1B. According to one embodiment of the present invention, fourth conductor 62 is joined to an electrode tip at second distal end 80, such as tip electrode 37 illustrated in FIG. 3 or tip electrode 95 illustrated in FIG. 4. Each conductor 71–74, corresponding with different electrodes must be electrically isolated from one another; according to one embodiment of the present invention, as illustrated in FIG. 1D, each conductor 71–74 includes an outer insulative layer 101–104.

FIG. 1D is a partial section plan view of the multi-conductor coil illustrated in FIG. 1C. A section through each conductor 71–74 in a segment 100 of coil 70, proximal to first electrode 76, is illustrated in FIG. 1D, shows insulative layers 101, 102, 103, and 104. According to embodiments of the present invention, insulative layers 101–104 are formed form a biocompatible, biostable, and durable insulative material, one example of which is a polyamide. Although all four conductors are illustrated in FIG. 1D as having an insulative layer, in an alternate embodiment, one of the four may be without an insulative layer. Surfaces of reverse wound portions of conductors 71, 72, and 73, are freed of insulative layers 101, 102, and 103 in order to form electrodes 76, 77, and 78 respectively. According to one embodiment of the present invention, a laser is used to remove the layers 101–103 away from the outer surfaces of conductors 71–73 according to methods well know to those skilled in the art.

FIG. 2A is a partial section plan view of an implantable lead 10 incorporating coil 50 from FIG. 1A, according to one embodiment of the present invention. As illustrated in FIG. 2A, lead 10 further includes a proximal end 30, a distal end 26, an outer insulative sheath 22, an inner tubing 23 forming a lumen 25. As illustrated in FIG. 2A, coil 50 extends around inner tubing and within outer insulative sheath 22 from a connector contact 31 at proximal end 30 to distal end 26 where electrode 53 is formed by reverse winding of conductor 51, as previously described, is disposed. In one embodiment, a fiber core 21, indicated by a dashed line, extends within lumen 25 from proximal end 30 to distal end 26 to strengthen lead 10; Williams and Chivers disclose embodiments of leads having a fiber core construction in U.S. Pat. No. 6,516,230, which is incorporated herein in its entirety. In an alternate embodiment, a stylet (not shown) is used to guide lead 10 via lumen 25 to an implant site and, in yet another embodiment, as illustrated in FIG. 2B, lumen 25 surrounds another conductor attached to a tip electrode. FIG. 2B is a cross-sectional plan view of a distal end of an alternate embodiment of a lead incorporating coil 50 from FIG. 1A. As illustrated in FIG. 2B, lead 15 further includes a cable conductor 32 extending from a proximal end (not shown), where it is joined to a second connector contact (not shown), through lumen 25 past distal end 26 of coil 50, where electrode 53 is formed, to a second distal end 16 where it is joined to a helical tip electrode 24. According to embodiments of the present invention, cable conductor 32 is joined to helical tip electrode 24 by means of welding, crimping, bonding with a conductive adhesive, or a combination thereof according to methods well known to those skilled in the art. As further illustrated in FIG. 2B, lead 15 includes an insulative spacer 27 electrically isolating tip electrode 24 from reverse wound electrode 53. Although tip electrode 24 is illustrated as a helix in FIG. 2B, various geometries of tip electrodes well known to those skilled in the art are contemplated for alternate embodiments of the present invention.

FIG. 3 is a cross-sectional plan view of a distal end of an alternate embodiment of a lead incorporating coil 60 from FIG. 1B. As illustrated in FIG. 3, a lead 35 includes coil 60 extending around inner tubing 23 and within outer insulative sheath 22 from a proximal end (not shown), where conductors 61 and 62 are each joined to a connector contact (not shown), to first distal end 65, where reverse wound electrode 64 is formed by conductor 61, and to second distal end 66, where conductor 62 is joined to a tip electrode 37. Lead 35 further includes an insulative spacer 38 including a set of tines 39 as a fixation means to hold tip electrode 37 at the implant site according to one embodiment of the present invention. In an alternate embodiment a helical electrode, such as electrode 24 illustrated in FIG. 2B, not requiring tines 39 since a helical construction provides fixation, is joined to conductor 62 at second distal end 66. Furthermore, an embodiment according to the present invention includes a tip electrode, such as tip electrode 37, without tines 39 or another fixation means. According to embodiments of the present invention, conductor 62 is joined to tip electrode 37 by means of welding, crimping, bonding with a conductive adhesive, or a combination thereof according to methods well known to those skilled in the art. According to one embodiment, lead 35 further includes fiber core 21 shown as a dashed line; fiber core 21 serves to strength lead 35 as previously described in conjunction with FIG. 2A FIG. 4 is a partial section plan view of a lead incorporating coil 70 from FIGS. 1C–D according to one embodiment of the present invention. As illustrated in FIG. 4, a lead 45 includes coil 70 extending around inner tubing 23 and within outer insulative sheath 22 from a proximal end 90, where conductors 71, 72, 73, and 74 are joined to connector contacts 91, 92, 93, and 94, respectively, to first distal end 79, where reverse wound electrode 76 is formed by conductor 71, and to a second distal end 80, where conductor 74 is joined to a helical tip electrode 95. In between first distal end 79 and second distal end 80, as further illustrated in FIG. 4, first intermediate electrode 77 and second intermediate electrode 78 are formed by reverse wound conductors 72 and 73, respectively, and insulative spacers 115, 116, and 117 are positioned between electrodes 76 and 77, 77 and 78, and 78 and 79, respectively. According to embodiments of the present invention, conductor 74 is joined to helical tip electrode 95 by means of welding, crimping, bonding with a conductive adhesive, or a combination thereof according to methods well known to those skilled in the art. Although tip electrode 95 is illustrated as a helix in FIG. 4, various geometries of tip electrodes well known to those skilled in the art are contemplated for alternate embodiments of the present invention.

In various embodiments of the leads presented in FIGS. 2A–4, outer insulative sheath 22, inner tube 23, and insulative spacers 27, 38, 115, 116, and 117 are formed from biocompatible and biostable insulative materials, examples of which are polyurethane and silicone. Fabrication and assembly methods for such sheaths, tubes, and spacers are well known to those skilled in the art of electrical lead construction. Lengths of electrodes and spacers depicted herein vary according to different embodiments of leads, examples of which will be schematically presented in FIGS. 5–8. A maximum outer diameter of embodiments range from approximately 0.025 inch to approximately 0.120 inch depending upon an inner diameter required for lumen 25 and a diameter of the wound conductor wires. It is contemplated that various lead constructions according to the present invention will include conductors including wires having diameters ranging between approximately 0.001 inch and approximately 0.010 inch, dependent upon electrical resistance requirements. Furthermore, in one embodiment a cross-section of conductor wires is substantially round while in an alternate embodiment a cross-section of conductor wires is substantially rectangular.

An inner diameter of lumen 25, for various embodiments according to the present invention, will range between approximately 0.005 inch and 0.050 inch; the inner diameter dependent upon the incorporation within lumen 25 of additional conductors or an elongated delivery tool, for example, a stylet, guide wire, or pull wire, or upon pressure requirements for delivery of agents, for example a drug or a contrast agent, through lumen 25. In the latter case, if lumen 25 is used to deliver an agent an opening in lumen is included in proximity to a distal end of the lead.

Figure 5:
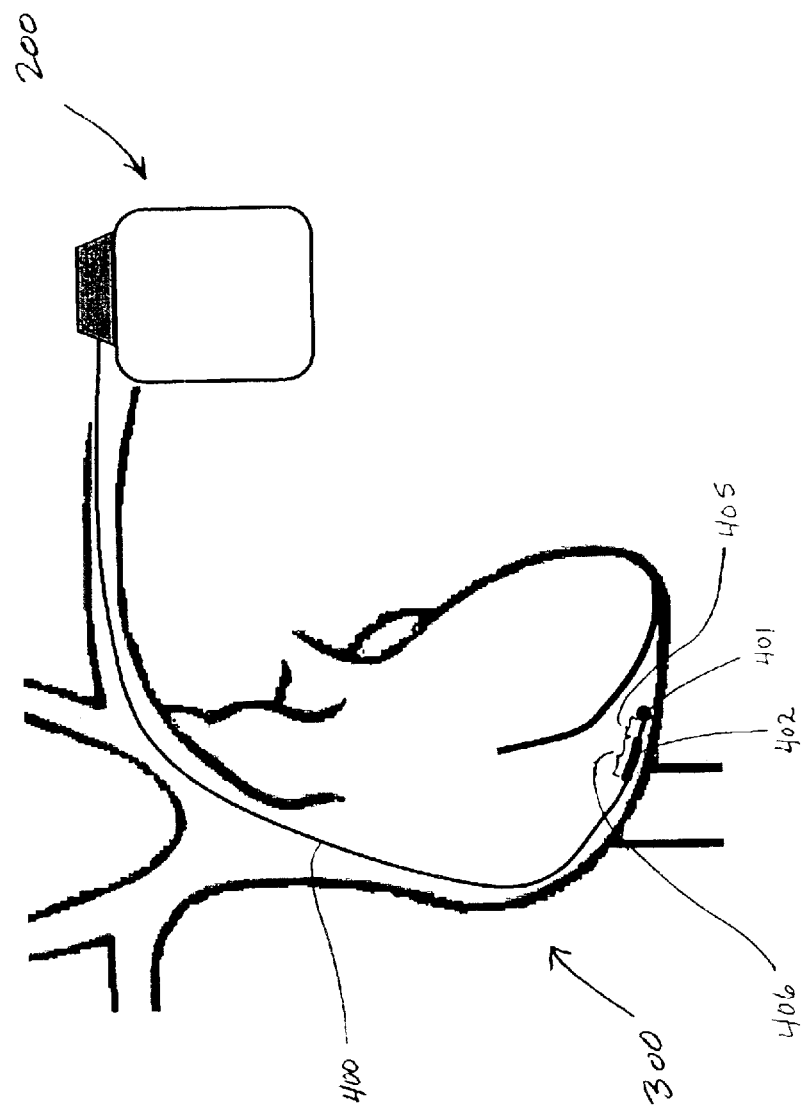

FIGS. 5–8 are schematics depicting several embodiments of implantable leads according to the present invention joined to an implantable medical device 200 and implanted in exemplary locations within a heart 300. As illustrated in FIG. 5, a lead 400 includes a tip electrode 401 and a reverse wound electrode 402 including a length 406 and spaced at a distance 405 from tip electrode 401. In one embodiment lead 400 incorporates coil 50 of FIG. 1A and in an alternate embodiment lead 400 incorporates coil 60 from FIG. 1B. According to embodiments of the present invention, length 406 is between approximately 2 millimeters and approximately 6 centimeters and distance 405 is between 4 millimeters and approximately 15 millimeters. According to one embodiment of the present invention, length 406 of reverse wound electrode 402 and spacing 405 are appropriate for electrode 402 to serve as a pace/sense anode in conjunction with tip electrode 401 (cathode), and, according to another embodiment length 406 and spacing 405 are appropriate for reverse wound electrode 402 to serve as a defibrillation electrode.

Figure 6:
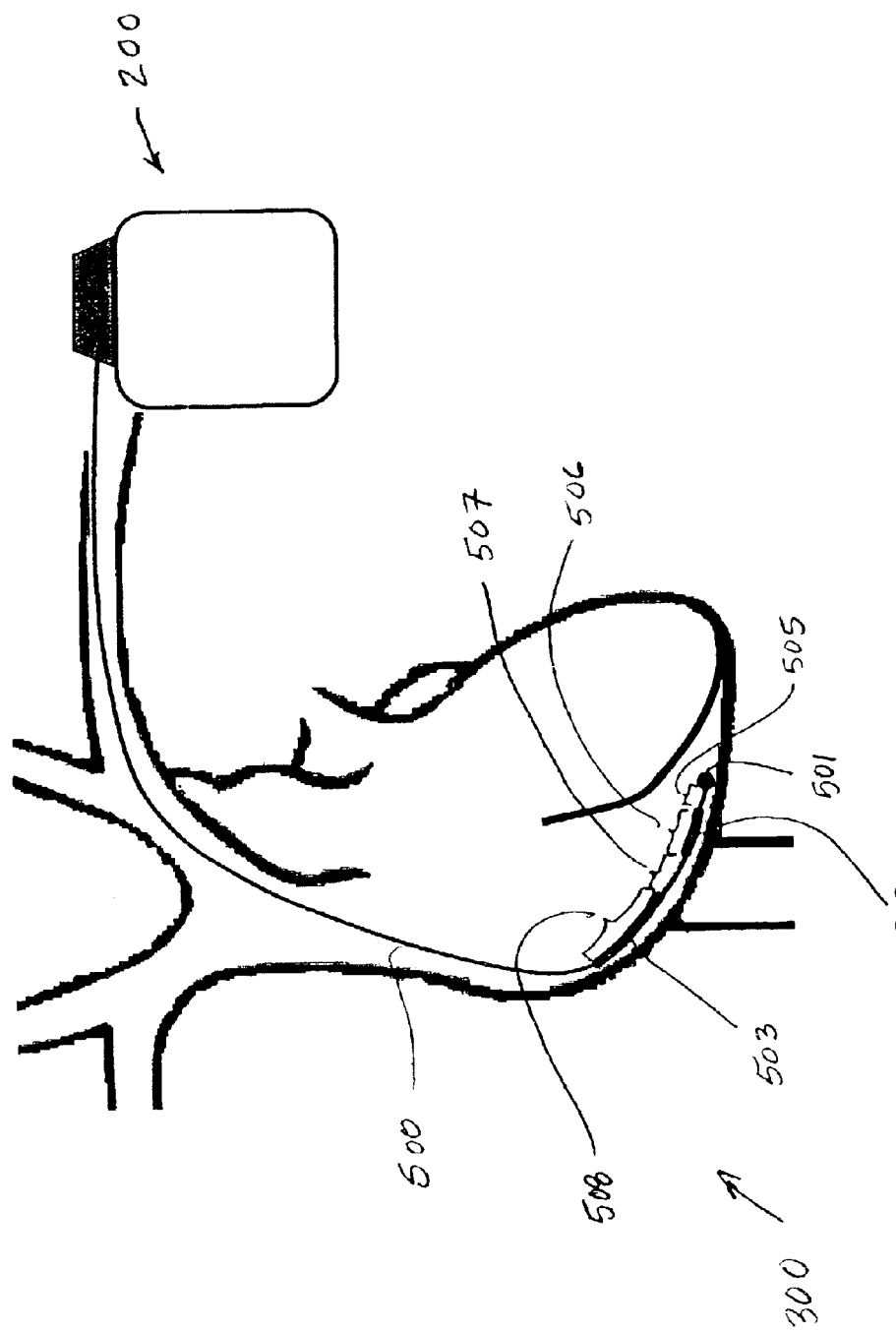

As illustrated in FIG. 6, a lead 500 includes a tip electrode 501, a first reverse wound electrode 502, including a length 506 and spaced at a distance 505 from tip electrode 501, and a second reverse wound electrode 503, including a length 508 and space at a distance 507 from first reverse wound electrode. In one embodiment, lead 500 includes a coil including a first and second conductor wherein both conductors are reverse wound, having a configuration similar to lead 15 shown in FIG. 2B in that tip electrode 501 is joined to a cable conductor; in another embodiment lead 500 includes a coil including a first, second and third conductor, having a configuration similar to lead 45 shown in FIG. 4 in that first and second conductors form reverse wound electrodes 503 and 502 while third conductor is joined to tip electrode 501. According to embodiments of the present invention, electrodes 502 and 503 have lengths 506 and 508 between approximately 2 millimeters and approximately 6 centimeters; distance 505 is between approximately 4 millimeters and approximately 10 millimeters; and distance 507 is between approximately 1 millimeter and 5 millimeters. According to one embodiment of the present invention, length 506 of electrode 502 is and distance 505 are appropriate for electrode 502 to serve as a pace/sense anode in conjunction with tip electrode 501 (cathode) and length 508 of electrode 503 and distance 507 are appropriate for electrode 503 to function as a defibrillation electrode. According to another embodiment, as illustrated in FIG. 7, distance 507 is increased so that reverse wound electrode 503 may positioned in another chamber of heart 300 or proximal to heart.

Figure 7:
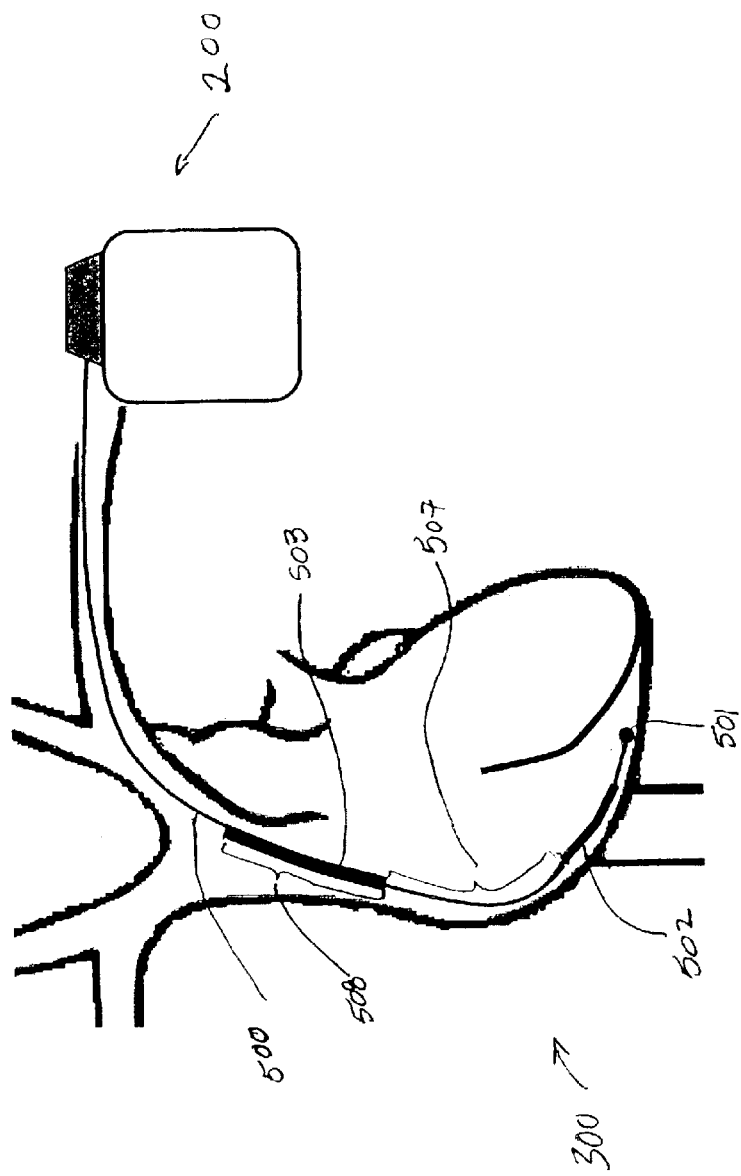

As illustrated in FIG. 8, a lead 700 includes all the elements of lead 500 from FIGS. 6 and 7 and further includes a third reverse wound electrode 704 spaced at a distance 705 from second reverse wound electrode 503 according to one embodiment of the present invention. In one embodiment lead 700 incorporates coil 70 of FIG. 1C. Distance 705 is such that reverse wound electrode may be positioned in an area of heart 300 separate from an area in which tip electrode 501 is positioned.

Finally, it will be appreciated by those skilled in the art of lead construction and implantation that the present invention can take many forms and embodiments and be applied in many more implant sites than those represented in FIGS. 5–8, such as epicardial sites and neuro-stimulation sites. The true essence and spirit of this invention are defined in the appended claims, and it is not intended that any embodiment of the invention presented herein should limit the scope thereof.

What is claimed is:

1. An implantable lead comprising:
   an insulative sheath; and
   a coil member extending through the insulative sheath and including first and second parallel conductors wound together to form interlaced coil windings;
   wherein the first conductor winds from a proximal end of the coil member to a first distal end section of the coil member and reverse winds back toward the proximal end to form a first electrode, and
   wherein the second conductor winds from the proximal end of the coil member to a second distal end section of the coil member and reverse winds back toward the proximal end to form a second electrode.

2. The implantable lead of claim 1, wherein a length of each of the first and second electrodes is between approximately 2 mm and 3 cm.

3. The implantable lead of claim 1, wherein a length of each of the first and second electrodes is between approximately 3 cm and 6 cm.

4. The implantable lead of claim 1, wherein the insulative sheath includes an outer diameter and the first electrode forms a second outer diameter of the coil member, the second outer diameter being substantially equal to the outer diameter of the insulative sheath.

5. The implantable lead of claim 1, further comprising
- an inner tubing forming a lumen and extending within the coil member from the proximal end to the second distal end section; and
- a fiber core extending within the lumen from the proximal end to the second distal end section where it is joined to an electrode tip.

6. The implantable lead of claim 1, wherein the coil member further includes a third conductor in parallel with the first and second conductors and wound together with them to form interlaced coil windings; the third conductor winding from the proximal end of the coil member to a location between the first distal end section and the second distal end section and reverse winding back toward the proximal end to form a third electrode at a location intermediate the first and second electrodes.

7. The implantable lead of claim 6, wherein the coil member further includes a fourth conductor in parallel with the first, second and third conductors and wound together with them to form interlaced coil windings; the fourth conductor winding from the proximal end of the coil conductor to a location between the first distal end section and the second distal end section and reverse winding back toward the proximal end to form a fourth electrode at a second location intermediate the first and second electrodes.

8. The implantable lead of claim 1, further comprising an insulated cable conductor extending from the proximal end of the coil member.

* * * * *